United States Patent [19]

Remy

[11] 4,160,031

[45] Jul. 3, 1979

[54] ANTIHISTAMINIC AND APPETITE STIMULATING 10,11-DIHYDRO-3-CARBOXYCYPROHEPTADINE

[75] Inventor: David C. Remy, North Wales, Pa.

[73] Assignee: Merck & Co., Inc., Rahway, N.J.

[21] Appl. No.: 743,562

[22] Filed: Nov. 22, 1976

Related U.S. Application Data

[63] Continuation of Ser. No. 563,285, Mar. 28, 1975, abandoned, and a continuation-in-part of Ser. No. 522,676, Nov. 11, 1974, abandoned.

[51] Int. Cl.$^2$ .................. A61K 31/445; C07D 211/34
[52] U.S. Cl. ............................. 424/267; 260/590 FB; 546/203; 546/204
[58] Field of Search .................. 260/293.62; 424/267; 546/203

[56] References Cited

U.S. PATENT DOCUMENTS

| | | | |
|---|---|---|---|
| 3,014,911 | 12/1961 | Engelhardt | 260/293 |
| 3,981,877 | 9/1976 | Prugh | 260/293.62 |

*Primary Examiner*—Natalie Trousof
*Assistant Examiner*—Richard A. Schwartz
*Attorney, Agent, or Firm*—William H. Nicholson; James A. Arno; Harry E. Westlake, Jr.

[57] ABSTRACT

10,11-Dihydro-3-carboxycyproheptadine is disclosed to have pharmaceutical utility as an appetite stimulant and as an antihistaminic agent. Also disclosed are processes for the preparation of such compound; pharmaceutical compositions comprising such compound; and methods of treatment comprising administering such compound and compositions.

5 Claims, No Drawings

ANTIHISTAMINIC AND APPETITE STIMULATING 10,11-DIHYDRO-3-CARBOXYCYPROHEPTADINE is a continuation, of application Ser. No. 563,285 filed Mar. 28, 1975 now abandoned, which in turn is a continuation-in-part of application Ser. No. 522,676, filed Nov. 11, 1974, now abandoned.

BACKGROUND OF THE INVENTION

This invention relates to 10,11-dihydro-3-carboxycyproheptadine (1-methyl-4-(3-carboxy-10,11-dihydro-5H-dibenzo[a,d]cyclohepten-5-ylidene)piperidine) as an appetite stimulant and as an antihistaminic agent; also contemplated within the scope of the present invention are the pharmaceutically acceptable salt, ester and amide derivatives of such compound. Further, this invention relates to processes for the preparation of such compounds; to pharmaceutical compositions comprising such compounds; and to methods of treatment comprising administering such compounds and compositions when an appetite stimulant and/or antihistamine effect is indicated. The free acid form of the 10,11-dihydro-3-carboxycyproheptadine of the present invention has the following structure formula (I):

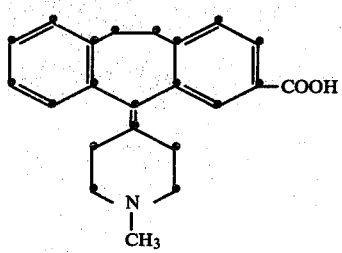

Unexpectedly, it has been discovered that the 10,11-dihydro-3-carboxycyproheptadines of the present invention are appetite stimulants and antihistaminics substantially devoid of other pharmacological effects such as anticholinergic activity, which latter activity is so characteristic of compounds structurally related to cyproheptadine, including dihydro derivatives thereof. Accordingly, it is an object of the present invention to provide 10,11-dihydro-3-carboxycyproheptadine and its pharmaceutically acceptable salt, ester and amide derivatives as appetite stimulants and antihistaminic agents. It is a further object of this invention to provide processes for the preparation of such compounds pharmaceutical compositions comprising such compounds; and methods of treatment comprising administering such compounds and compositions when an appetite stimulant and/or antihistaminic effect is indicated.

DETAILED DESCRIPTION OF THE INVENTION

The 10,11-dihydro-3-carboxycyproheptadines of the present invention may conveniently be prepared from 3-bromo-10,11-dihydro-5H-dibenzo[a,d]cyclohepten-5-one (see, for example, U.S. Pat. Nos. 3,306,934 and 3,014,911 which patents are incorporated herein by reference) by reaction with 1-methyl-4-piperidylmagnesium halide in a suitable solvent such as tetrahydrofuran and the like to provide 1-methyl-4-(3-bromo-10,11-dihydro-5-hydroxy-5H-dibenzo-[a,d]cyclohepten-5-yl)-piperidine, which is dehydrated on treatment with a suitable dehydrating agent such as a mineral acid and the like to provide 1-methyl-4-(3-bromo-10,11-dihydro-5H-dibenzo[a,d]cyclohepten-5-ylidene)piperidine, which on conversion to the 3-cyano species by treatment with cuprous cyanide followed by hydrolysis yields the desired 1-methyl-4-(3-carboxy-10,11-dihydro-5H-dibenzo[a,d]cyclohepten-5-ylidene)piperidine-(10,11-dihydro-3-carboxycyproheptadine) of the present invention. The following diagram illustrates this process:

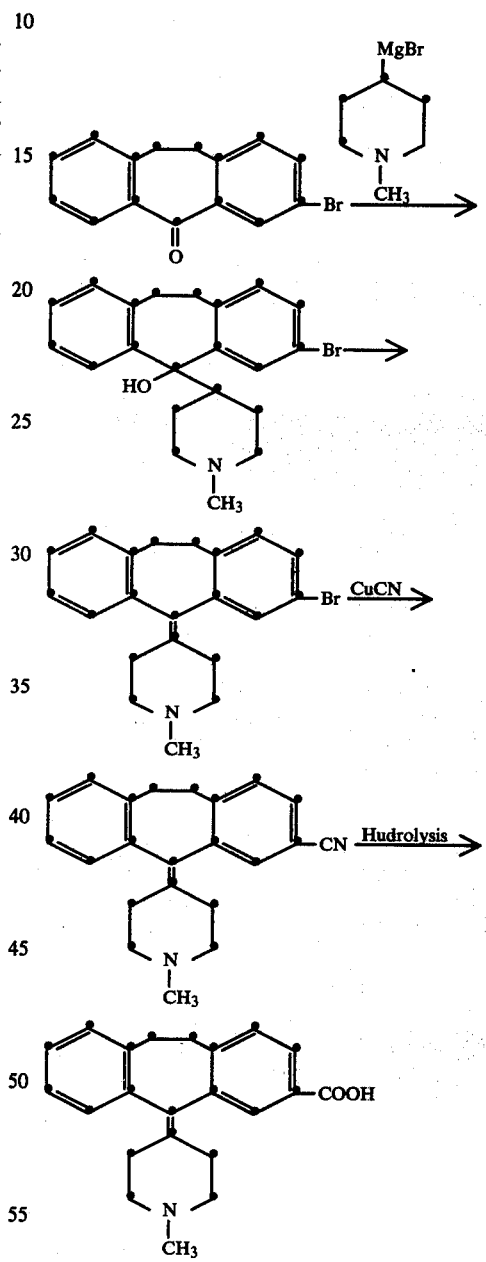

Suitable pharmaceutical salt, ester and amide forms of the 10,11-dihydro-3-carboxycyproheptadine of the present invention may be prepared by conventional means. Salt forms are the most preferred and include (relative to the nitrogen atom of the piperidyl moiety): the hydrochloride, sulfate, phosphate, citrate, tartrate, succinate and the like; with respect to salts based upon the carboxy function, salts derived from the alkali and alkaline earth metals such as sodium and potassium are preferred. These salts are generally equivalent in potency to the free acid form taking into consideration the stoichiometric quantities employed.

In the method of treatment and pharmaceutical composition aspects of the present invention it is noted that the precise unit dosage form and dosage level depend upon the case history of the individual being treated and consequently are left to the discretion of the therapist. In general, however, the compounds of the present invention produce the desired effect of appetite stimulation when given at from about 0.01 to about 10.0 mg. per kg. body weight per day. The preferred form of delivery of the instant compounds for appetite stimulation of domestic animals is by solution in drinking water or preformulated feedstuffs. For human and animal administration, any of the usual pharmaceutical oral forms may be employed such as tablets, elixirs and aqueous suspensions comprising from about 0.01 to about 10.0 mg. of the compounds of this invention per kg. body weight given daily. Thus, for example, tablets given 2-4 times per day comprising from about 0.5 to about 50 mg. of the compounds of this invention are suitable for human treatment. Sterile solutions (representatively given for human treatment) for injection comprising from about 0.1 to about 10.0 mg. of the compounds of this invention given two to four times daily are also suitable means of delivery. When an antihistaminic effect is indicated, the above-recited dosage forms and levels are also appropriate.

The following examples representatively illustrate but do not limit the product, compositional or method of treatment aspect of the present invention.

EXAMPLE 1

Preparation of 1-methyl-4-(3-carboxy-10,11-dihydro-5H-dibenzo[a,d]cyclohepten-5-ylidene)piperidine Step A:
1-Methyl-4-(3-bromo-10,11-dihydro-5H-dibenzo[a,d]cyclohepten-5-ylidene)piperidine To an ice-cooled solution of 15.0 gm. (0.0523 mole) of 3-bromo-10,11-dihydro-5H-dibenzo[a,d]cyclohepten-5-one in 150 ml. of dry tetrahydrofuran is added dropwise over 0.5 hr., 100 ml. of 0.53M 1-methyl-4-piperidylmagnesium chloride in tetrahydrofuran. The solution is stirred for one hour, and then the tetrahydrofuran is removed on a rotary evaporator. The red-oily residue that remains is dissolved in benzene and water is added dropwise until a clear benzene supernatant and a gelatinous aqueous phase is obtained. The benzene is decanted and the gelatinous aqueous phase is extracted with two 100 ml. portions of hot benzene. The combined benzene phases are washed with six 200 ml. portions of water and then the benzene phase is evaporated on a rotary evaporator. The residue that remains is triturated with acetonitrile. The crystalline product is removed by filtration, washed with additional acetonitrile, collected and dried at 60° C. The product 1-methyl-4-(3-bromo-10,11-dihydro-5-hydroxy-5H-dibenzo[a,d]cyclohepten-5-yl)piperidine, 9.66 gm. (65%), melts at 203°-207° C.

A mixture of 9.66 gm. of 1-methyl-4-(3-bromo-10,11-dihydro-5-hydroxy-5H-dibenzo[a,d]cyclohepten-5-yl)piperidine and 130 ml. of 6N hydrochloric acid is stirred and refluxed for 0.5 hr. The bulk of the hydrochloric acid is removed on a rotary evaporator and the residue is partitioned between 5% aqueous sodium hydroxide and ether. The ether phase is removed, washed with water, dried over magnesium sulfate, filtered, and the ether removed to give 9.17 gm. of 1-methyl-4-(3-bromo-10,11-dihydro-5H-dibenzo[a,d]cyclohepten-5-ylidene)piperidine.

Step B:
1-Methyl-4-(3-cyano-10,11-dihydro-5H-dibenzo[a,d]cyclohepten-5-ylidene)piperidine A mixture of 9.17 gm. (0.0249 mol) of 1-methyl-4-(3-bromo-10,11-dihydro-5H-dibenzo[a,d]cyclohepten-5-ylidene)piperidine, 4.58 gm. (0.0498 mol) of cuprous cyanide, and 30 ml. of dry dimethylformamide is stirred and heated under reflux for 6.5 hr. To the cooled solution (25° C.) is added 54 ml. of water, 27 ml. of a saturated aqueous solution of sodium cyanide, and 75 ml. of benzene. The mixture is stirred until a two phase system is obtained. The benzene phase is removed and the aqueous phase is extracted with two 75 ml. portions of benzene. The combined benzene phases are washed with 100 ml. of aqueous 0.1M sodium cyanide, three 100 ml. portions of water, and dried over magnesium sulfate. After filtering, evaporation of the benzene gives 7.40 gm. of a crystalline residue. This material is dissolved in the minimum volume of chloroform and passed over an alumina column (15"×1") packed in chloroform. The column is eluted with chloroform. Evaporation of the chloroform gives a crystalline product that is recrystallized from isopropyl alcohol to give pure 1-methyl-4-(3-cyano-10,11-dihydro-5H-dibenzo[a,d]-cyclohepten-5-ylidene)piperidine, m.p. 152°-154° C.

Analysis Calc. for: $C_{22}H_{22}N_2$:
Calc.: C, 84.04; H, 7.05; N, 8.91. Found: C, 83.87; H, 7.41; N, 8.73.

Step C:
1-Methyl-4-(3-carboxy-10,11-dihydro-5H-dibenzo[a,d]cyclohepten-5-ylidene)piperidine hydrochloride A mixture of 1.0 gm. (0.00318 mol) of 1-methyl-4-(3-cyano-10,11-dihydro-5H-dibenzo[a,d]cyclohepten-5-ylidene)piperidine and 20 ml. of 6N hydrochloric acid is stirred and refluxed for 18 hours. After cooling, the mixture is filtered, and the collected solid is washed with 6N hydrochloric acid and then with ethanol. The dried material weighs 1.03 gm. (87%). Recrystallization from absolute ethanol gives pure 1-methyl-4-(3-carboxy-10,11-dihydro-5H-dibenzo[a,d]cyclohepten-5-ylidene)piperidine hydrochloride, m.p. 304°-307° C.

Analysis Calc. for: $C_{22}H_{23}NO_2.HCl$:
Calc.: C, 71.43; H, 6.54; N, 3.79; Cl, 9.59. Found: C, 71.01; H, 6.87; N, 3.73; Cl, 9.44.

EXAMPLE 2

Pharmaceutical compositions

A typical tablet containing 1 mg. 1-methyl-4-(3-carboxy-10,11-dihydro-5H-dibenzo[a,d]cyclohepten-5-ylidene)piperidine per tablet is prepared by mixing together with the active ingredient calcium phosphate, lactose and starch in the amounts shown in the tables below. After these ingredients are thoroughly mixed, the appropriate amount of magnesium stearate is added and the dry mixture blended for an additional three minutes. This mixture is then compressed into tablets weighing approximately 124 mg. each. Similarly prepared are tablets containing 1-methyl-4-(3-carboxy-10,11-dihydro-5H-dibenzo[a,d]cyclohepten-5-ylidene)-piperidine hydrochloride.

| TABLET FORMULA | |
|---|---|
| INGREDIENT | MG. PER TABLET |
| 1-Methyl-4-(3-carboxy-10,11-dihydro-5H-dibenzo[a,d]cyclohepten-5-ylidene)-piperidine | 1 mg. |
| Calcium phosphate | 52 mg. |
| Lactose | 60 mg. |
| Starch | 10 mg. |
| Magnesium stearate | 1 mg. |
| 1-Methyl-4-(3-carboxy-10,11-dihydro-5H-dibenzo[a,d]cycloheten-5-ylidene)-piperidine hydrochloride | 1 mg. |
| Calcium phosphate | 52 mg. |
| Lactose | 60 mg. |
| Starch | 10 mg. |
| Magnesium stearate | 1 mg. |

What is claimed is:

1. 10,11-Dihydro-3-carboxycyproheptadine or a nontoxic pharmaceutically acceptable salt thereof.

2. A pharmaceutical composition for stimulating appetite comprising an effective appetite stimulating amount in unitary dosage form of 10,11-dihydro-3-carboxycyproheptadine or a nontoxic pharmaceutically acceptable salt thereof and a pharmaceutical carrier therefor.

3. A pharmaceutical composition for inducing an antihistaminic effect comprising an effective antihistaminic amount in unitary dosage form of 10,11-dihydro-3-carboxycyproheptadine or a nontoxic pharmaceutically acceptable salt thereof and a pharmaceutical carrier therefor.

4. A method of stimulating appetite comprising administering to a patient in need of such treatment an effective appetite stimulating amount of 10,11-dihydro-3-carboxycyproheptadine or a nontoxic pharmaceutically acceptable salt thereof.

5. A method of inducing an antihistaminic effect comprising administering to a patient in need of such treatment an effective antihistaminic amount of 10,11-dihydro-3-carboxycyproheptadine or a nontoxic pharmaceutically acceptable salt thereof.

* * * * *